Figure 1:
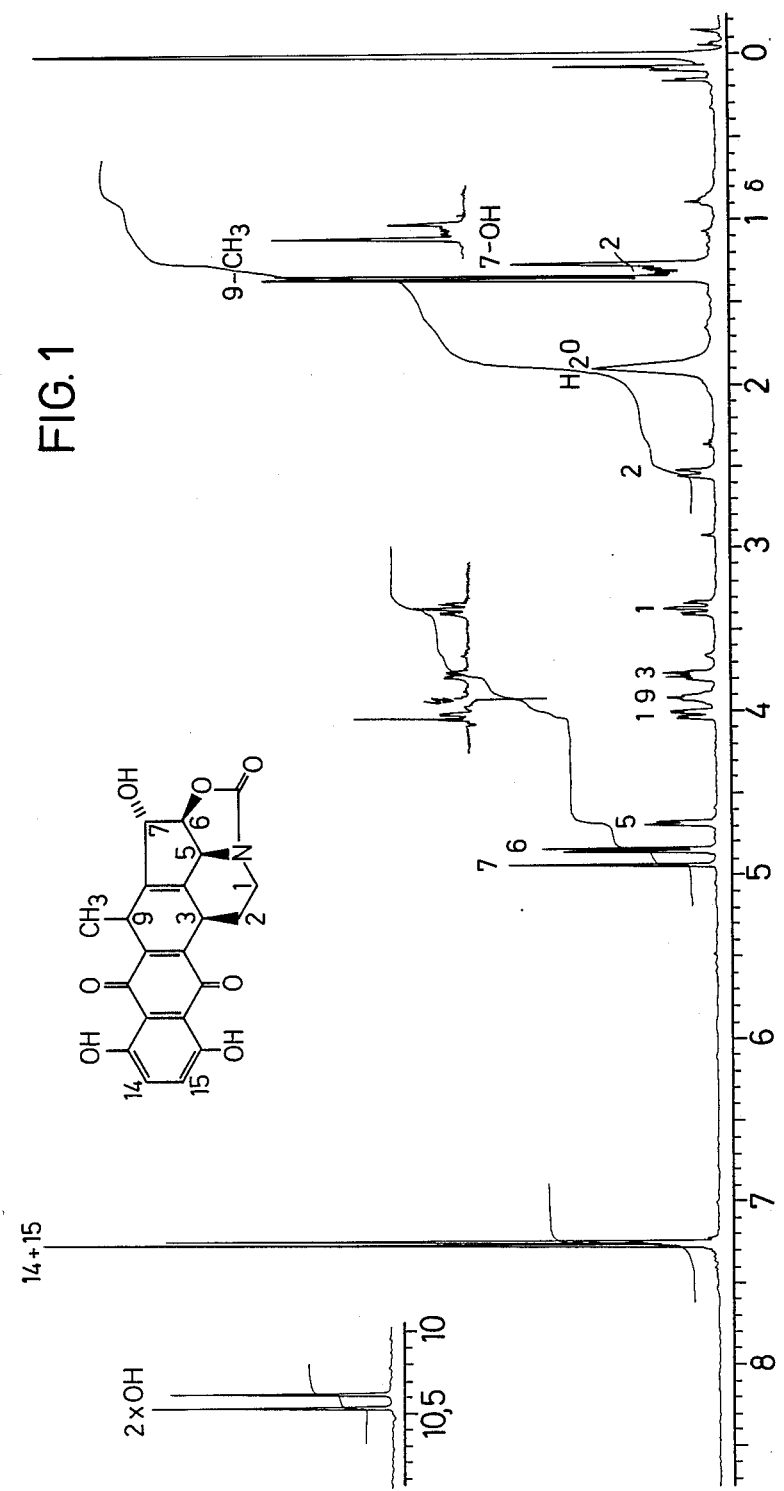

United States Patent [19]

Hoppe et al.

[11] Patent Number: 4,849,409

[45] Date of Patent: Jul. 18, 1989

[54] DIELS-ALDER ADDUCT FROM STREPTAZOLINE AND NAPHTHOQUINONES AND ITS OXIDATION PRODUCTS, WHICH HAVE CYTOTOXIC AND ANTIMICROBIAL ACTIVITY AND WHICH ACT AGAINST PROTOZOA

[75] Inventors: Hans-Ullrich Hoppe, Hofheim am Taunus; Susanne Grabley, Königstein/Taunus; Hartmut Voelskow, Battersheim am Main; Merten Schlingmann, Königstein/Taunus; Hans P. Kraemer, Marburg; Matthias Wiesner, Mainz; Joachim Thiem, Münster, all of Fed. Rep. of Germany

[73] Assignee: Hoechst Aktiengesellschaft, Frankfurt am Main, Fed. Rep. of Germany

[21] Appl. No.: 48,954

[22] Filed: May 12, 1987

[30] Foreign Application Priority Data

May 14, 1986 [DE] Fed. Rep. of Germany ....... 3616180

[51] Int. Cl.$^4$ ..................... A61K 31/47; C07D 498/06
[52] U.S. Cl. ....................................... 514/27; 514/63; 514/279; 536/17.4; 546/14; 546/41
[58] Field of Search .................. 546/41, 14; 514/279, 514/63, 27; 536/17.4

[56] References Cited

PUBLICATIONS

Grabley, et al., Angew. Chem., vol. 99(7), pp. 692–693 (1987).
Drautz, et al., Chemical Abstracts, vol. 96:16990r (1982).
Kozikowski, et al., J. Am. Chem. Soc., vol. 107(6), pp. 1763–1765 (1985).
Fuson, "Reactions of Organic Compounds", John Wiley & Sons, Inc. New York (1962) pp. 683–685, 697.
A. Karrer and M. Dobler, "X-Ray Analysis of O-Acetyl Dihydro-Strepatzoline", Helv. Chim. Acta, vol. 65 (5) 1432–1435 (1982).

*Primary Examiner*—Donald G. Daus
*Assistant Examiner*—Diana G. Rivers
*Attorney, Agent, or Firm*—Finnegan, Henderson, Farabow, Garrett, & Dunner

[57] ABSTRACT

Streptazoline is reacted with naphthoquinones in a Diels-Alder reaction, and the adduct is then oxidized. The resulting compounds have cytotoxic activity, in particular against leukemia cells, and have an antimicrobial action and act against protozoa.

7 Claims, 3 Drawing Sheets

DIELS-ALDER ADDUCT FROM STREPTAZOLINE AND NAPHTHOQUINONES AND ITS OXIDATION PRODUCTS, WHICH HAVE CYTOTOXIC AND ANTIMICROBIAL ACTIVITY AND WHICH ACT AGAINST PROTOZOA

Cancerous diseases currently represent one of the greatest challenges to medicine. In the majority of cancer patients, surgical operations and radiotherapy are inadequate because, owing to the formation of metastases, there is no point in local control of the tumor. In this stage of the disease, only cancer chemotherapy still offers hope of a cure. Hence there is an increase in interest in suitable new compounds with as few side effects as possible. According to a compilation of the National Cancer Institute in the USA, at present there are about 50 natural materials or derivatives of natural materials in clinical use for cancer chemotherapy, and approximately a further 100 are in various phases of clinical development. Among these, there is particular interest in the anthracyclines whose cytotoxic activity has been systematically investigated for about 25 years.

The present invention describes compounds having cytotoxic properties and prepared by derivatization of streptazoline.

Streptazoline (compound of the formula IV, $R^3=H$) was isolated by Zähner et al. [Helv. Chim. Acta 64, 1752 (1981)] as a secondary metabolite from *Streptomyces viridochromogenes*, and its structure was elucidated by Keller-Schierlein et al. [Helv. Chim Acta 65, 1432, (1982)]. The total synthesis of streptazoline was described by Kozikowski et al. [JACS 107, 1763, (1984)].

Streptazoline is only a very weak antibiotic and has no cytotoxic action. Reaction of the compound, or of its derivatives corresponding to the formula IV, with naphthoquinones results in products which can be further oxidized to give derivatives of 1,4-dihydroanthraquinone or anthraquinone. Both the Diels-Alder adducts and their oxidation products have cytotoxic and antimicrobial properties and act against protozoa.

Thus the invention relates to:

1. The compound of the general formula I

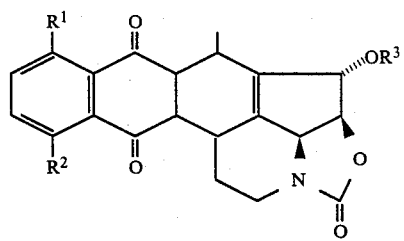

in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

2. The compound of the general formula II

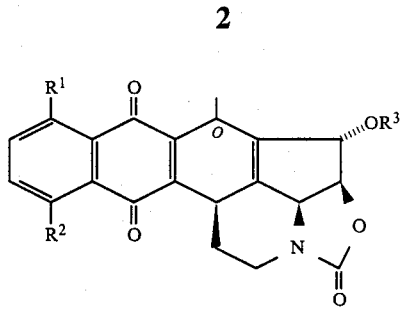

in which the two possible epimers at the position labeled "o" occur, and in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

3. The compound of the general formula III

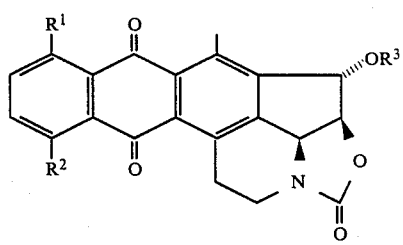

in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

4. A process for the preparation of the compound of the general formula I, which comprises reacting together the compound of the formula IV

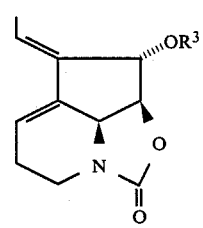

in which $R^3$ denotes hydrogen, acetyl, trimethylsilyl, dimethyl-tertiary-butylsilyl or glucosyl, and the compound of the general formula V

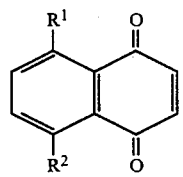

in which $R^1$ and $R^2$, independently of one another, denote hydrogen, hydroxyl, methoxy, O-acetyl or O-benzyl.

5. A process for the preparation of the compounds of the general formulae II and III, which comprises oxidation of the compound of the general formula I.

6. The use of the compound of the general formula I, II or III as an agent having cytotoxic activity.

7. The use of the compound of the general formula I, II or III as an antimicrobial or an agent acting against protozoa.

Streptazoline ($R^3=H$) can be obtained from Streptomycetes by methods known per se. This compound and its derivatives, which are represented by the general formula IV, are added as the conjugated diene in a Diels-Alder reaction onto the dienophile of the general formula V. The reaction takes place in a closed vessel at elevated temperatures of about 60° to 140° C. in inert solvents and is complete after 4 to 15 hours have elapsed. Examples of suitable solvents are toluene, nitrotoluene, xylene, benzene, tetrahydrofuran or chloroform. Particularly good results are obtained when the reactants are mixed in toluene at 100° to 120° C. Alternatively, it also is possible to react the reactants IV and V in methylene chloride or chloroform with the addition of Lewis acids such as, for example, aluminum trichloride or titanium tetrachloride, at temperatures between $-20°$ and $+10°$ C., if $R^1$ and $R^2$ are not hydroxyl, and $R^3$ is not hydrogen. The relevant solvents and catalysts are then removed from the reaction mixtures. The compound I can be purified by chromatographic methods.

The compound of the general formula I serves as an intermediate for the preparation of the compounds of the general formulae II and III. The latter are obtained by oxidation of the regio- or diastereomeric compound of the general formula I in alkaline mixtures of ($C_1$-$C_4$)-alcohols and water. In general, the oxidation takes place particularly preferably with atmospheric oxygen at temperatures of 10° to 40° C. in a solution of water and methanol, whose mixing ratio is in the range 20:1 to 1:20. The pH is adjusted to between 9 and 14 with an alkali, in particular sodium hydroxide solution, potassium hydroxide solution and carbonate solutions, pyridine or ammonia. It is also possible, in the case of compounds I sensitive to hydrolysis (for example $R^1=R^2=$O-acetyl, and $R^3=$acetyl), for the oxidation to be carried out in anhydrous methanol with pyridine and pure oxygen.

Under the conditions described, there is preferential formation, as has been established by NOE measurements, of the compound II in the depicted configuration, it being possible for both epimers at the position labeled "o" to occur.

It has been demonstrated that the compound of the general formula II is not an intermediate on the route to the compound of the general formula III, because it is impossible to prepare III from II by renewed application of the oxidizing conditions described above.

The compounds of the general formulae I, II and III have a cytotoxic action, in particular against leukemia cells. In addition, the compounds have an antimicrobial, in particular antifungal, action, particularly preferentially against *Candida albicans,* and an action against protozoa, in particular agains *Trichomonas vaginalis.*

The invention is illustrated in detail in the examples which follow. The percentage data relate to weight.

EXAMPLE 1

400 mg of streptazoline ($R^3=H$) (1.93 mmol) and 367 mg of naphthazarin ($R^1=R^2=$OH) (1.93 mmol) in 100 ml of toluene are stirred in a closed vessel at 100° to 120° C. for 10 to 12 hours. The solvent is then removed from the reaction mixture in vacuo, and the residue is chromatographed on silica gel 60 (Merck) in chloroform/methanol (95/5). Apart from unreacted streptazoline and naphthazarin there are obtained 500 mg of a mixture of the colorless Diels-Alder adducts which strongly fluoresce at 366 nm. It is possible to drive the reaction to completion if a two-fold excess of the dienophile is used.

EXAMPLE 2

The process is carried out as in Example 1 but naphthoquinone ($R^1=R^2=H$) is used in place of naphthazarin. The corresponding Diels-Alder adducts are obtained in analogous yields.

EXAMPLE 3

The Diels-Alder adducts obtained from Example 1 are stirred in a mixture of 20 ml of water, 60 ml of methanol and 20 ml of 2N sodium hydroxide solution in the air at room temperature for a period of 10 to 15 minutes. This solution is then adjusted to pH 1 with aqueous hydrochloric acid and extracted 3 times with chloroform. The organic phase is dried over sodium sulfate, and the solvent is removed in vacuo. There are obtained 450 mg (59% based on streptazoline) of the compound of the formula II, in which $R^1$ and $R^2$ denote hydroxyl, and $R^3$ denotes hydrogen, and 30 mg (4% based on streptazoline) of the compound of the formula III in which $R^1$, $R^2$ and $R^3$ have the specified meaning. FIG. 1 shows the $^1$H NMR spectrum of the compound II with $R^1=R^2=$hydroxyl, and $R^3=$hydrogen.

EXAMPLE 4

Figure 2:
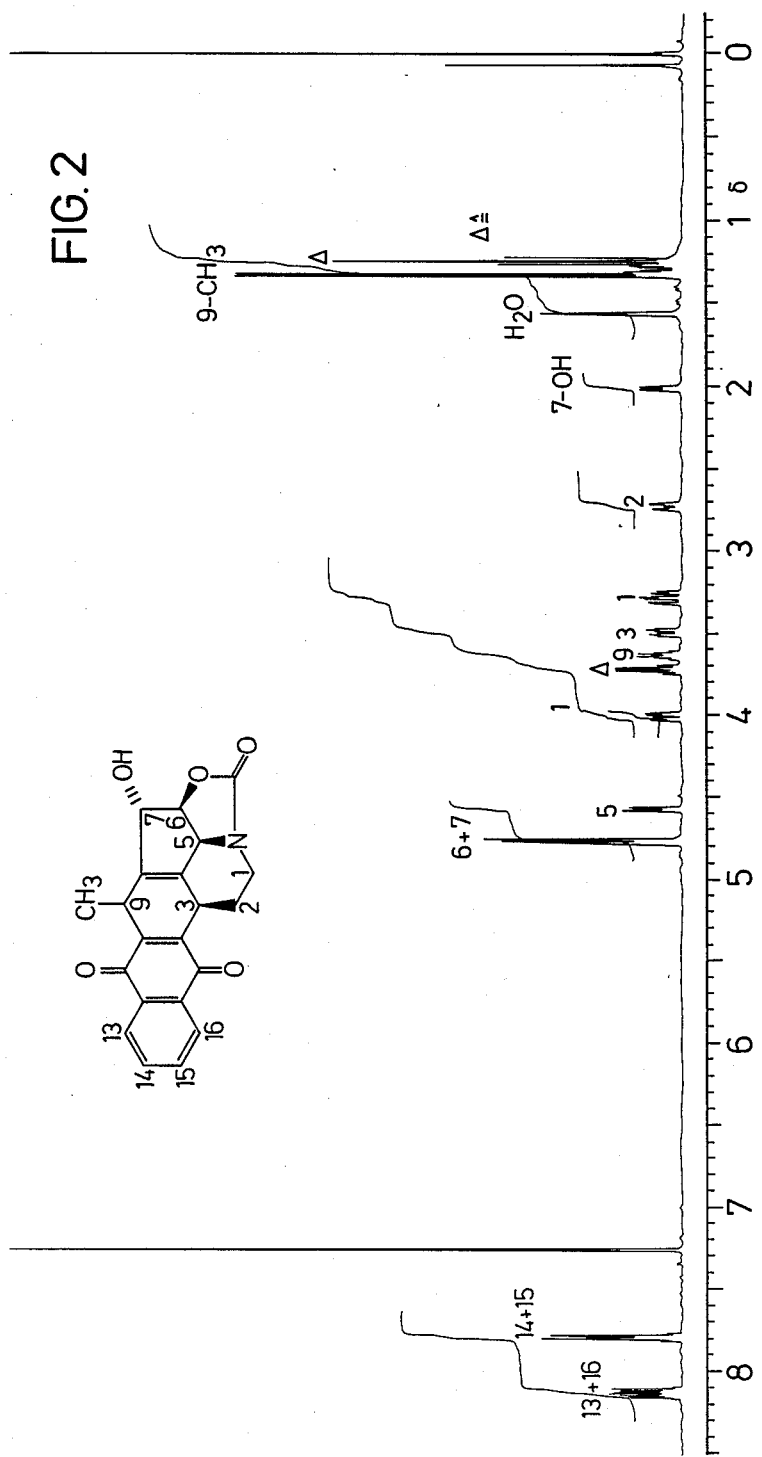
Figure 3:
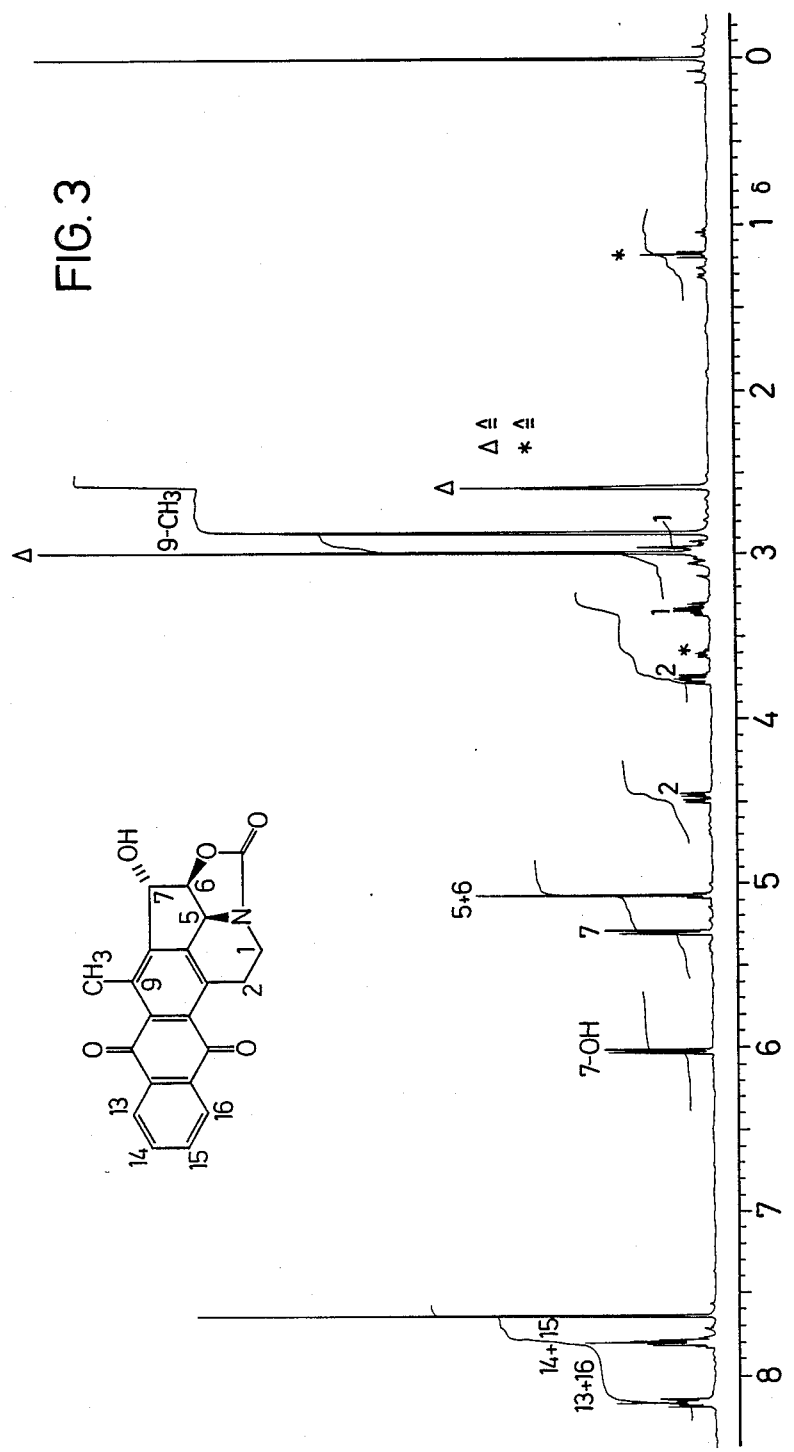

The process is carried out as in Example 3, but the Diels-Alder adducts obtained from Example 2 are used. There are obtained 233 mg (31% based on streptazoline) of the compound of the formula II in which $R^1$, $R^2$ and $R^3$ denote hydrogen, and 149 mg (20% based on streptazoline) of the compound III in which $R^1$, $R^2$ and $R^3$ have the specified meaning. FIGS. 2 and 3 show the $^1$H NMR spectra of the said compounds.

EXAMPLE 5

400 mg of streptazoline dimethyl-tertiary-butylsilyl ether (1.24 mmol) and 196.11 mg (1.24 mmol) of 1,4-naphthoquinone and 165.34 mg of $AlCl_3$ in 40 ml of methylene chloride are stirred at 0° C. in a closed vessel for 30 minutes. The reaction mixture is then partitioned between $H_2O$ and methylene chloride, and the organic phase is dried over sodium sulfate. After the solvent has been removed in vacuo, the residue is chromatographed on silica gel 60 in chloroform/methanol (95:5). 535 mg of Diels-Alder adducts are obtained (90% based on streptazoline dimethyl-tertiary-butylsilyl ether).

EXAMPLE 6

The Diels-Alder adducts obtained as in Example 5 are stirred in a mixture of 200 ml of methanol and 15 ml of 2N sodium hydroxide solution in the air at room temperature for a period of 15 minutes. This solution is then adjusted to pH 3 with aqueous hydrochloric acid and is extracted 3 times with chloroform. After drying over $Na_2SO_4$, chromatography on silica gel 60 in chloroform/methanol (95:5) is carried out.

477 mg of compound III ($R^1=R^2=H$, $R^3=$dimethyl-tertiary-butylsilyl, 90% based on the Diels-Alder adducts used) are obtained.

EXAMPLE 7

Demonstration of the cytotoxic action:

The cytotoxic action of the compounds can be established in various test systems such as, for example, in the soft agar colony test on mouse leukemia cells in vitro. Formation of colonies of L1210 leukemia cells in soft agar:

This method serves to demonstrate the effect of the test substances on the growth behavoir of the cells over several generations (with a cell cycle lasting 10–12 hours, about 14 successive generations are observed in the 7 days the test lasts). In this test, substances having cytostatic activity bring about a reduction in the observed number of colonies compared with an untreated control. The details of the test procedure are as follows:

500 L1210 leukemia cells per plate are incubated with various concentrations of the compound of the formula II, obtained as in Example 3, as test substance at 37° C. for 1 hour. The cells are then washed twice with McCoy 5A medium and finally, after addition of 0.3% agar, poured into Petri dishes. Controls are incubated merely with fresh medium. In addition, in place of the incubation for 1 hour, various concentrations of the test substance are admixed to the upper agar layer, in order thus to acheive continuous exposure of the cells throughout the incubation time. After the agar has solidified, the plates are incubated in an incubator at 37° C. for 7 days (5% $CO_2$, 95% relative humidity). The number of resultant colonies with a diameter $>60\mu$ is then counted. The results are expressed as the quotient of the number of colonies on treated agar plates and the number of colonies on the untreated control. The $IC_{50}$ was obtained, as a measure of the activity of the test substance, from the dose-effect curve thus obtained. The comparison substance used in this test is the cytostatic adriamycin. The results are compiled in the table.

TABLE

| Substance | Stem cell assay cont. $IC_{50}$ (μg/ml) | Stem cell assay 1 h $IC_{50}$ (μg/ml) |
|---|---|---|
| Test substance | 0.04 | 0.26 |
| Streptazoline | 10 | 10 |
| Adriamycin | 0.02 | 0.04 |

Assessment:

As the table shows, the compound of the formula II obtained as in Example 3 has a cytotoxicity comparable to that of adriamycin, whereas the starting compound streptazoline has no cytotoxicity worthy of note.

We claim:

1. The compound of the formula I

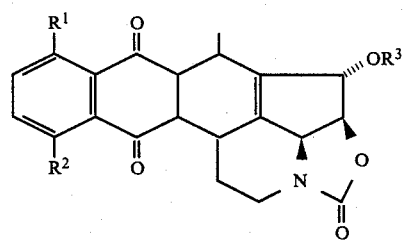

in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

2. The compound of the formula II

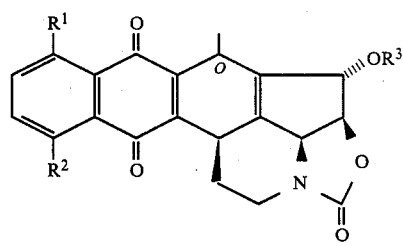

in which the two possible epimers at the position labeled "o" occur, and in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

3. The compound of the formula III

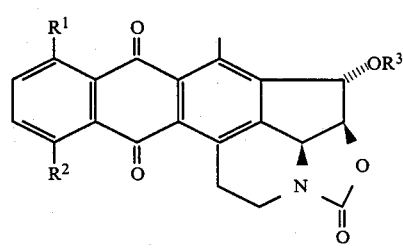

in which $R^1$ and $R^2$, independently of one another, denote hydrogen, hydroxyl, methoxy, O-acetyl or O-benzyl, and $R^3$ denotes hydrogen, acetyl, trimethylsilyl, dimethyl-tertiary-butylsilyl or glucosyl.

4. Pharmaceutical composition having antimicrobial action and being active against protozoa, comprising an effective amount of the compound of the general formula I and/or II and/or III

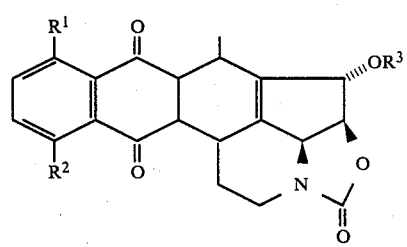

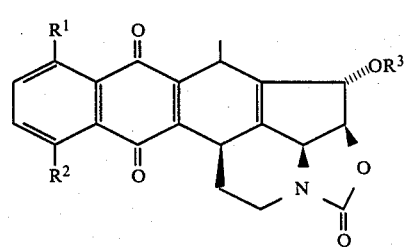

-continued

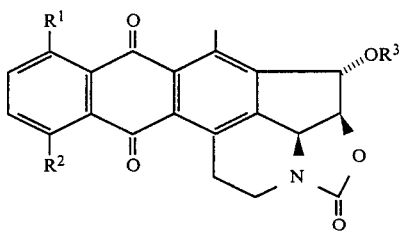

in which R¹ and R², independently of one another, denote hydrogen, hydroxy, methoxy, O-acetyl or O-benzyl, and R³ denoted hydrogen, acetyl, trimethylsiyl, dimethyl-tertiary-butylsilyl or glucosyl and a pharmaceutically acceptable carrier.

5. Method of treating infectious diseases, wherein an effective amount of the compound of the general formula I and/or II and/or III is administered

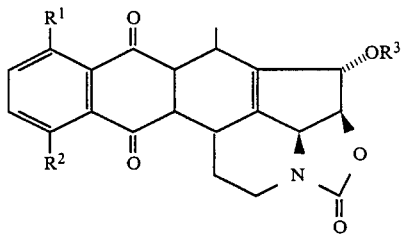

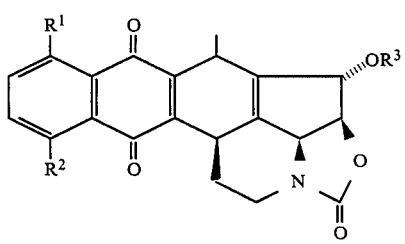

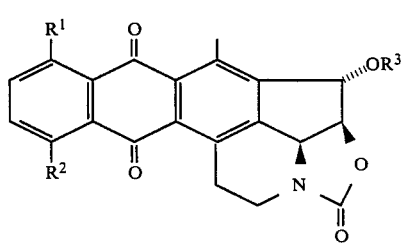

in which R¹ and R², independently of one another, denote hydrogen, hydroxy, methoxy, O-acetyl or O-benzyl, and R³ denotes hydrogen, acetyl, trimethylsilyl, dimethyl-tertiary-butylsilyl or glucosyl, as antimicrobials and agents against protozoa.

6. A pharmaceutical composition useful for the treatment of leukemia cells which comprises, as active ingredient, an effective amount of the compound of the general formula I and/or II and/or III

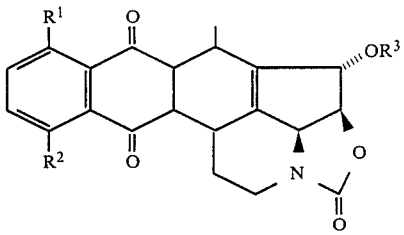

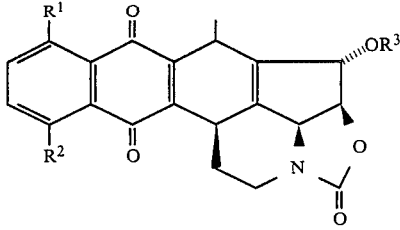

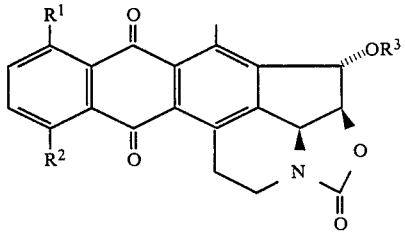

in which R¹ and R², independently of one another, are hydrogen, hydroxy, methoxy, O-acetyl or O-benzyl, and R³ is hydrogen, acetyl, trimethylsilyl, dimethyl-tertiary-butylsilyl or glucosyl in association with with a pharmaceutical acceptable carrier.

7. A method of inhibiting the growth of leukemia cells wherein an effective amount of the compound of the general formula I and/or II and/or III

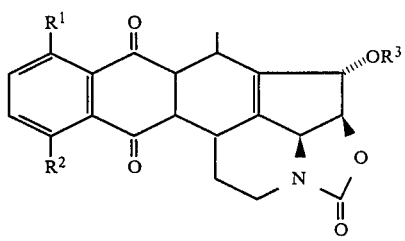

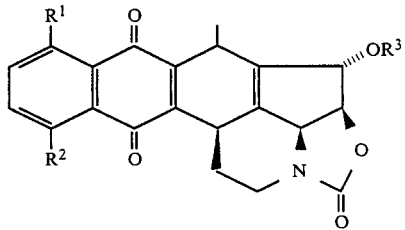

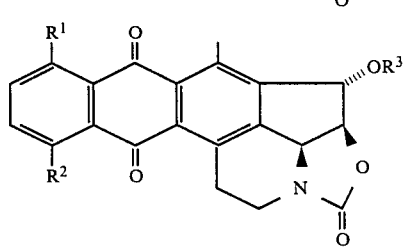

is administered in which R¹ and R², independently of one another are hydrogen, hydroxy, methoxy, O-acetyl or O-benzyl and R³ is hydrogen, acetyl, trimethylsilyl, dimethyl-tertiary-butylsilyl or glucosyl.

* * * * *

UNITED STATES PATENT AND TRADEMARK OFFICE
CERTIFICATE OF CORRECTION

PATENT NO. : 4,849,409

DATED : July 18, 1989

INVENTOR(S) : Hans-Ullrich Hoppe et al

It is certified that error appears in the above-identified patent and that said Letters Patent is hereby corrected as shown below:

Claim 4, column 7, line 16, change "denoted"
to --denotes--.

Claim 4, column 7, line 16, change "trimethylsiyl"
to --trimethlsilyl--.

Claim 5, column 7, line 62, "agents" should
be followed by --acting--.

Claim 6, column 8, line 34, change "pharmaceutical"
to --pharmaceutically--.

Signed and Sealed this

Twenty-third Day of October, 1990

Attest:

HARRY F. MANBECK, JR.

*Attesting Officer*      *Commissioner of Patents and Trademarks*